US005271929A

United States Patent [19]

Hashiguchi et al.

[11] Patent Number: 5,271,929

[45] Date of Patent: Dec. 21, 1993

[54] NUCLEAR MAGNETIC RESONANCE IMAGING AGENT COMPRISING A DI-ALDEHYDE COMPLEX

[75] Inventors: Yuji Hashiguchi, Soedgaura; Kumiko Iwai, Ichihara; Shigemi Seri, Ichihara; Susumu Kondo, Ichihara; Makoto Azuma, Ichihara, all of Japan

[73] Assignee: Nihon Medi-Physics Co., Ltd., Hyogo, Japan

[21] Appl. No.: 910,546

[22] Filed: Jul. 8, 1992

[30] Foreign Application Priority Data

Jul. 15, 1991 [JP] Japan .................................... 173743

[51] Int. Cl.[5] .................. G01N 24/08; A61K 31/715; C08B 35/08; C07H 23/00

[52] U.S. Cl. .......................................... 424/9; 514/54; 514/57; 514/59; 514/836; 436/173; 128/653.4; 534/16; 536/104; 536/105

[58] Field of Search .................... 424/9; 536/104, 105; 514/54, 57, 59, 836; 436/173; 128/653.14, 654; 534/16

[56] References Cited

U.S. PATENT DOCUMENTS

| | | | |
|---|---|---|---|
| 4,671,958 | 6/1987 | Robwell et al. | 424/85 |
| 4,678,667 | 7/1987 | Meares et al. | 424/85 |
| 4,965,007 | 10/1990 | Yudelson | 252/62.53 |
| 5,057,302 | 10/1991 | Johnson et al. | 424/1.1 |
| 5,143,716 | 9/1992 | Unger | 424/9 |

FOREIGN PATENT DOCUMENTS

| | | |
|---|---|---|
| 0186947 | 7/1986 | European Pat. Off. . |
| 345723 | 12/1989 | European Pat. Off. . |
| 481420 | 4/1992 | European Pat. Off. . |
| WO85/05554 | 12/1985 | PCT Int'l Appl. . |
| WO87/02893 | 5/1987 | PCT Int'l Appl. . |
| WO90/03802 | 4/1990 | PCT Int'l Appl. . |

OTHER PUBLICATIONS

Patent Abstracts of Japan, vol. 10, No. 36, (Feb. 1986), abstract of JP-A-60 186 502.

Patent Abstracts of Japan, vol. 8, No. 222, (Oct. 1984), abstract of JP-A-59 106 425.

Weinmann, H. J., et al., Physiological Chemistry and Physics and Medical NMR, 16, 167-172 (1984).

Ogan, Marc D., et al., Investigative Radiology, vol. 22, 665-671 (Aug. 1987).

Wang, S., et al., Radiology 1990: 175:483-488.

*Primary Examiner*—Glennon H. Hollrah
*Assistant Examiner*—Gary E. Hollinden

[57] ABSTRACT

There is disclosed a nuclear magnetic resonance imaging agent comprising a complex compound composed of (a) a dialdehyde-saccharide having a molecular weight of from 500 to 10,000, at least one of the constituent monosaccharides of which is oxidation-cleaved, (b) at least one complexing agent which is chemically coupled to an aldehyde group of the dialdehyde-saccharide and (c) a paramagnetic metal ion which is chemically coupled to the complexing agent.

8 Claims, 1 Drawing Sheet

NUCLEAR MAGNETIC RESONANCE IMAGING AGENT COMPRISING A DI-ALDEHYDE COMPLEX

FIELD OF THE INVENTION

The present invention relates to a nuclear magnetic resonance imaging (hereinafter sometimes abbreviated as MRI) agent, in particular, to a nuclear magnetic resonance diagnostic agent containing a paramagnetic metal species.

BACKGROUND OF THE INVENTION

Diethylenetriaminepentaacetic acid-gadolinium (DTPA-Gd) is the only one pharmaceutical for use as an MRI agent for which effectiveness as a diagnostic agent in the brain or spinal regions, has almost been established. However, since it is rapidly excreted in the urine after administration, its half-life period in the blood is extremely short, such as about 14 minutes [Hiroki Yoshikawa et al., Gazoshindan, 6, 959–969 (1986)]. Therefore then, it is difficult to make several diagnoses (blood vessel distribution, blood stream distribution, distribution volume, permeation and the like in a lesion) with a single injection. Furthermore, since it is nonspecifically distributed from the interior of a blood vessel to the interstices of tissue cells, sometimes, no clear contrast can not be obtained due to indistinguishable difference in the concentration between normal tissue and a lesion.

Furthermore, since the imaging time in a nuclear magnetic resonance diagnosis method depends upon the magnetic field used in the MRI spectrometer a longer imaging time is required, for example, in the case of using the widely popular low magnetic field. In such case, the condition of a lesion cannot be precisely understood on using DTPA-Gd which disappears from the blood within a short period of time. Thus, diagnosis with DTPA-Gd is naturally limited depending upon the diagnosing site or the particular type of a diagnosing apparatus.

In order to solve these problems, there has been an increased demand for an MRI agent which can localize in a blood vessel for a constant period of time from immediately after administration, stays therein for a relatively longer period of time and has a medium or long half-life period in blood. As a result, paramagnetic metal complex compounds using as their carriers polymer materials such as HSA [Ogan, M. D. et al., Invest Radiol., 22, 665–671 (1987)], dextran [Brasch, R. C. et al., Radiology, 175, 483–488 (1990)], polylysine (JP-A 64-54028) and the like have been studied and developed as prototype imaging agents. However, since all these carriers are polymer compounds having a molecular weight of tens of thousands or more, retention time in the blood is unnecessarily long as from ten and several hours to several days and there are problems with residence in the body and antigenicity and the like.

OBJECTS OF THE INVENTION

The main object of the present invention is to provide an MRI agent containing a paramagnetic metal ion and having appropriate localization in a blood vessel and appropriate retention in blood. In other words, the technical problem to be solved by the present invention is to improve retention of DTPA-Gd in the blood among the various behaviors of DTPA-Gd in the body. Accordingly, for the imaging agent of the present invention it is required that (1) it stay in the blood and not permeate out of a blood vessel, (2) it is excreted mainly and relatively rapidly into the urine, (3) it hardly accumulates in the body, and (4) it has nonantigenicity and low toxicity.

This object as well as other objects and advantages of the present invention will become apparent to those skilled in the art from the following description with reference to the accompanying drawings.

SUMMARY OF THE INVENTION

Figures 1, 2, 3:
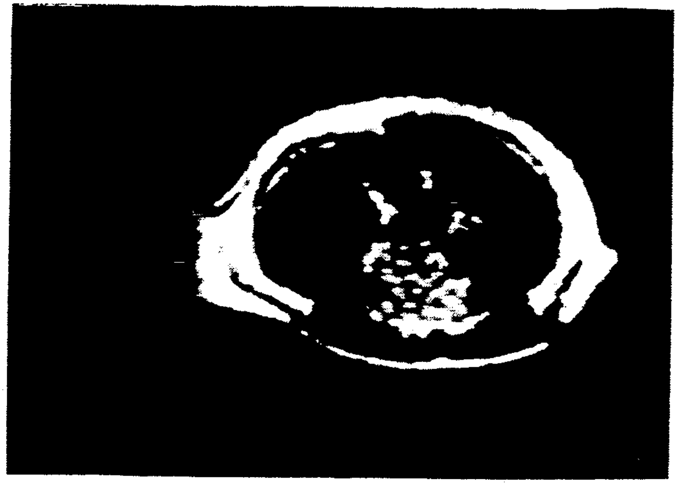
FIG. 1 is an MRI showing a transverse view of the chest region including the heart of a rat sacrificed immediately after administration of a (dialdehyde-starch)-p-aminobenzyl-DTPA-Gd (DAS-DTEN-Gd) solution.
FIG. 2 is an MRI showing a transverse view of the chest region including the heart of a rat sacrificed 30 minutes after administration of a DAS-DTEN-Gd solution.
FIG. 3 is an MRI showing a transverse view of the chest region including the heart of a rat sacrificed 30 minutes after administration of DTPA-Gd (MAGNEVIST).

According to the present invention, there is provided a nuclear magnetic resonance imaging agent which comprises a complex compound composed of (a) a dialdehyde-saccharide having a molecular weight of from 500 to 10,000, at least one of the constituent monosaccharides of which is oxidation-cleaved, (b) at least one complexing agent which is chemically coupled to an aldehyde group of the dialdehyde-saccharide and (c) a paramagnetic metal ion which is chemically coupled to the complexing agent.

DETAILED DESCRIPTION OF THE INVENTION

In order to accomplish the above objects and to solve the above problems, the present inventors have carried out an intense study. As a result, it has been found that a complex compound obtained by chemically coupling a paramagnetic metal ion through a complexing agent which is chemically coupled to a certain dialdehyde-saccharide is suitable for a nuclear magnetic resonance diagnostic agent which satisfies the above demands. Furthermore, it has been found that such diagnostic agent improves retention of DTPA-Gd in the blood and has a clinically effective half-life period in the blood.

For example, in the case of (dialdehyde-starch)-DTEN-In-111 and (dialdehyde-amylose)-DTEN-In-111 composed of dialdehyde-starch (average molecular weight: 7,000, hereinafter abbreviated as DAS) and dialdehyde-amylose (average molecular weight: 2,900, hereinafter abbreviated as DAA) as the dialdehyde-saccharide, p-aminobenzyl-DTPA [Martin, W. B. et al, Inorg. Chem., 25, 2772–2781 (1986)] (hereinafter abbreviated as DTEN) as the complexing agent, radioactive In-111 as the metal species (the use of a radioactive metal species in place of a paramagnetic metal ion results from handling restrictions and is a conventional experimental procedure in this art field), the half-life periods in the blood in a rat are calculated as 2 hours and 45 minutes, respectively, based on the radioactivity distribution ratio in the blood with time after intravenous injection. This supports that these compounds show the effective retention in the blood which is clinically required. Furthermore, the excretion of these compounds into the urine at 24 hours after administration is calculated as 78% /dose and 87% /dose, respectively, based on the above radioactivity distribution experiment. In view of this, it is clear that these compounds have good excretion properties. Furthermore, from this experiment, it has been confirmed that these compounds have no problems in specific distribution and residence in the body.

The present invention was completed based on the above finding and, as described above, the gist thereof is an MRI agent which comprises a complex compound composed of (a) a dialdehyde-saccharide having a molecular weight of from 500 to 10,000, at least one of the constituent monosaccharides of which is oxidation-cleaved, (b) at least one complexing agent which is chemically coupled to an aldehyde group of the dialdehyde-saccharide and (c) a paramagnetic metal ion which is chemically coupled to the complexing agent.

As described above, in the case of the conventional prototype paramagnetic metal complex imaging agents using polymer materials such as HSA, dextran, polylysine and the like having the molecular weight of tens of thousands or more, the the retention in the blood is considerably improved. However, their disappearance half-life periods in blood are unnecessarily long and residence thereof in the body also causes trouble. These result in the clinical disadvantage that administration cannot be repeated, and the like. Furthermore, in view of safety, chemical toxicity due to the compound per se and, in some cases, metal toxicity due to the paramagnetic metal ion released from the complexing agent during residence for a long period of time are not negligible. Thus, various drawbacks are recognized in the use of the polymer materials composed of polymerized of repeting units.

On the other hand, since an oxidation-cleaved dialdehyde-saccharide having a molecular weight of from 500 to 10000 is used as a parent skeleton, the present invention has been successful in providing a clinically useful imaging agent which has no such drawbacks and solves the abovedescribed problems.

The dialdehyde-saccharide to be used as the above component (a) in the complex compound of the imaging agent of the present invention, has a molecular weight of from 500 to 10,000, preferably, not more than 3,000, and is preferably an oxide of an oligosaccharide which is tri- to deca-saccharide. Examples of the dialdehyde-saccharide include maltotriose, maltotetraose, maltopentaose, maltohexaose, maltoheptaose, isomaltotriose, isomaltotetraose, isomaltopentaose, isomaltohexaose, isomaltoheptaose, cellotriose, cellotetraose, cellopentaose, cellohexaose, laminaritriose, laminaritetraose, laminaripentaose, laminarihexaose, laminariheptaose, cyclodextrin, amylose (average molecular weight: 2,900), dextran (average molecular weight: 2,000 to 8,000), starch (average molecular weight: 7,000) and the like. Preferred for use is a dialdehyde-saccharide obtained by oxidation of the constituent monosaccharide, D-glucose. The oxidation-cleavage can be carried out according to a known method, for example, using sodium periodate.

As the complexing agents of the above component (b), there can be used a linear or cyclic polyaminopolycarboxylic acid having an active amino group as a crosslinking chain and a bifunctional structure which is capable of trapping a metal ion to form a complex, preferably, a bifunctional complexing agent having an active amino group and a DTPA (diethylenetriaminepentaacetic acid) skeleton or a DOTA (1,4,7,10-tetraazacyclododecane-1,4,7,10-tetraacetic acid) skeleton. Examples of the complexing agent include 1-(p-aminobenzyl)diethylenetriaminepentaacetic acid [Martin, W. B. et al., Inorg Chem , 25, 2772–2781 (1986)], 2-(p-aminobenzyl)-1,4,7,10-tetraazacyclododecane-1,4,7,10-tetraacetic acid (U.S. Pat. No. 4,678,667), 2-aminobutyl-1,4,7,10-tetraazacyclododecane-1,4,7,10-tetraacetic acid [Parker, D. et al., Pure & Appl. Chem., 61, 1637–1641 (1989)] (hereinafter abbreviated as "AB-DOTA") and the like.

The oxidation-cleaved dialdehyde-saccharide is coupled with the complexing agent according to a known method. For example, the dialdehyde-saccharide is reacted with the complexing agent in an alkaline solution to —CH=N—. If necessary, the compound can be reduced to convert —CH=N— into —$CH_2$—NH—.

The paramagnetic metal ion for the component (c) can be selected from lanthanide elements having the atomic number ranging from 57 to 70 and is preferably Gd or Dy. The paramagnetic metal can be a lanthanide element per se or a compound containing such an element, for example, a chloride or oxide. The complexing can be carried out according to a conventional method.

The complex compound thus obtained has a structure where at least one, preferably, two or more complexing agents are chemically coupled to the dialdehyde-saccharide having a molecular weight of from 500 to 10,000, at least one, preferably, two or more of the constituent monosaccharides of which are oxidation-cleaved, and the paramagnetic metal ion is coupled to the complexing agent portion.

The above-described complex compound can be optionally admixed with one or more pharmaceutically acceptable additives by a conventional method to prepare an imaging agent in various suitable forms. Preferably, the complex compound is dissolved in an aqueous physiologically acceptable solvent to prepare an imaging agent in the form of a solution.

For using the complex compound of the present invention as a MRI agent, administration is in a dose ranging from 0.0001 to 10 mmol/kg, preferably, from 0.005 to 0.5 mmol/kg, as the dose for the paramagnetic metal ion. It is usually administered intravenously. In some cases, it can be administered orally or intra-arterially.

Retention in the blood of the complex compound of the present invention is from 0.5 to 5 hours as the half-life period in the blood. Therefore, the compound can be appropriately selected and used with a particular retention in the blood and with a particular kind of MRI spectrometer where the magnetic field tends to be diversified. For example, in the case of a low magnetic field MRI spectrometer, it is preferred to use an imaging agent having a relatively long retention in the blood so as to promote collection efficiency for proton relaxation of the imaging agent. When the complex compound of the present invention contains Gd as the paramagnetic metal ion, since the effect on shortening of the relaxation time per the Gd ion is predominantly stronger than that of DTPA-Gd, it can be used more advantageously than DTPA-Gd. Furthermore, in a diagnosis with a low magnetic field MRI spectrometer having lower collection efficiency for proton relaxation effect, detection efficiency is increased in another sense and thereby the imaging time can be shortened. Furthermore, when it is desired to obtain the same contrast effect as that in DTPA-Gd with the same magnetic field, the complex compound of the present invention can be used in a less amount than DTPA-Gd and therefore is also advantageous from the stand point of safety. Contrary to this, in the case of the same dose, the complex compound of the present invention can provide much more information about a living body when used as the imaging agent and thereby its clinical usefulness is improved. Accordingly, the present invention can provide an imaging agent having appropriate retention in the blood and effectively enhanced effect, which matches the magnetic field of an MRI spectrometer or imaging conditions.

Since the complex compound of the present invention has appropriate retention in blood and localization in a blood vessel, a blood vessel distribution image (vascularity) can be evaluated. Therefore, the imaging agent of the present invention is also expected to be useful as a transvenous imaging agent for MR angiography which has remarkably advanced.

Furthermore, since the complex compound of the present invention is hydrophilic, it can be used as is, to prepare a concentrated solution. In the case of DTPA-Gd, the addition of a certain solubilizer is required for the preparation of a solution having a desired concentration. Accordingly, when a solution is prepared containing the same concentration of Gd as that of DTPA-Gd is prepared, in some cases, the complex compound of the present invention does not require any solubilizer. Further, since the complex compound of the present invention is polynuclear, when the same concentration of Gd solution is prepared, the total number of moles becomes small, resulting in decrease in the osmotic pressure. Thus, the complex compound of the present invention is also advantageous from the pharmaceutical viewpoint.

As described hereinabove, the imaging agent of the present invention comprises a complex compound composed of a specific dialdehyde-saccharide, a complexing agent which is chemically coupled to an aldehyde group of the dialdehyde-saccharide and a paramagnetic metal ion which is chemically coupled to the complexing agent. Thus, by using this novel and specific complex compound, a clinically effective retention time in the blood and an enhanced contrast effect in the magnetic field employed in MRI, can be realized.

The following Examples, Tests and Reference Examples further illustrate the present invention in detail but are not be construed to limit the scope thereof.

EXAMPLE 1

Synthesis of DAS-DTEN

Starch (average molecular weight: 7,000) was oxidation-cleaved with periodic acid according to a conventional method to obtain DAS.

DAS (0.5 g, 0.07 mmol) was dissolved in 0.1M phosphate buffer (pH 7.0, 50 ml), followed by addition of DTEN (0.8 g, 1.6 mmol). Triethylamine (1.66 g, 16.4 mmol) was added thereto and the pH was adjusted to about 12. The mixture was reacted with stirring at room temperature for 24 hours. To the reaction mixture was added sodium borohydride (0.121 g, 3.2 mmol) and the mixture was further reacted with stirring at room temperature for another 24 hours. The pH was adjusted to 2 or below with addition of 7N hydrochloric acid and then the mixture was neutralized with addition of 10N aqueous solution of sodium hydroxide to obtain crude DAS-DTEN.

A part of the reaction mixture (50 μl) was removed and admixed with 0.1M citrate buffer (pH 5.9, 100 μl) and indium chloride (In-111) solution (50 μl). The ratio of DAS-DTEN-In-111 and DTEN-In-111 was determined by thin layer chromatography, and it was confirmed that 6.4 molecules of DTEN were coupled per one molecule of DAS.

The above reaction mixture was purified by gel filtration chromatography (Sephadex G-75) to obtain DAS-DTEN (0.57 g).

Proton-NMR spectrum (solvent/$D_2O$, 270 MHz): 2.10–3.33 (10 H, m, $CH_2$), 3.37–4.11 (m, CH and $CH_2$), 4.30 (1 H, m, N—CH), 6.80 (2 H, d, benzene ring), 7.08 (2 H, d, benzene ring).

IR absorption spectrum (KBr tablet method): 780 $cm^{-1}$ (CH in benzene ring), 1100 $cm^{-1}$ (OH), 1410 $cm^{-1}$ ($CH_2$), 1615 $cm^{-1}$ (COOH)

EXAMPLE 2

Synthesis of DAA-DTEN

Amylose (average molecular weight: 2,900) was oxidation-cleaved by periodic acid according to a conventional method to obtain DAA.

DAA (0.5, 0.17 mmol) was dissolved in 0.1M phosphate buffer (pH 7.0, 50 ml), followed by addition of DTEN (0.678 g, 1.4 mmol). The pH was adjusted to about 12 with addition of triethylamine (1.4 g, 13.8 mmol). The mixture was treated in the same manner as in Example 1, to obtain crude DAA-DTEN.

A part of the reaction mixture (50 μl) was removed and admixed with 0.1M citrate buffer (pH 5.9, 100 μl) and indium chloride (In-111) solution (50 μl). The ratio of DAA-DTEN-In-111 and DTEN-In-111 was determined by thin layer chromatography and it was confirmed that 2.1 molecules of DTEN were coupled per one molecule of DAA.

The above reaction mixture was purified by gel filtration chromatography (Sephadex G-75) to obtain DAA-DTEN (0.32 g).

Proton-NMR spectrum (solvent/$D_2O$, 270 MHz): 2.45–3.40 (10 H, m, $CH_2$), 3.45–4.52 (m, CH and $CH_2$), 4.36 (1 H, m, N—CH), 6.86 (2 H, d, benzene ring), 7.13 (2 H, d, benzene ring)

EXAMPLE 3

Synthesis of dialdehyde-maltopentaose (DAMP)-DTEN

Maltopentaose (molecular weight: 828) was oxidation-cleaved by periodic acid according to a conventional method to obtain DAMP.

DAMP (0.127 g, 0.15 mmol) was dissolved in 0.1M phosphate buffer (pH 7.0, 5 ml), followed by addition of DTEN (0.296 g, 0.6 mmol). The pH was adjusted to about 12 with addition of triethylamine (0.6 g, 6.0 mmol), and the mixture was treated in the same manner as in Example 1 to obtain crude DAMP-DTEN.

A part of the reaction mixture (50 μl) was removed and admixed with 0.1M citrate buffer (pH 5.9, 100 μl) and indium chloride (In-111) solution (50 μl). The ratio of DAMP-DTEN-In-111 and DTEN-In-111 was determined by thin layer chromatography, and it was confirmed that 1.2 molecules of DTEN were coupled per one molecule of DAMP.

The above reaction mixture was purified by gel filtration chromatography (Sephadex G-75) to obtain DAMP-DTEN (0.047 g).

Proton-NMR spectrum (solvent/$D_2O$, 270 MHz): 2.24–3.40 (10 H, m, $CH_2$), 3.40–4.13 (m, CH, $CH_2$ and NH), 4.28 (1 H, bs, N—CH), 6.78 (d, benzene ring), 7.05 (dd, benzene ring)

IR absorption spectrum (KBr tablet method): 810 $cm^{-1}$ (CH in benzene ring), 1080 $cm^{-1}$ (OH), 1400 $cm^{-1}$ ($CH_2$), 1630 $cm^{-1}$ (COOH)

EXAMPLE 4

Synthesis of DAMP-(AB-DOTA)

DAMP-(AB-DOTA) is obtained in the same manner as described in Example 3 except that AB-DOTA is used instead of DTEN.

EXAMPLE 5

Synthesis of DAS-DTEN-Gd

DAS-DTEN (0.7 g, 0.07 mmol) was dissolved in distilled water (3 ml). Gadolinium chloride hexahydrate (0.024 g, 0.066 mmol) was added thereto, and the mixture was reacted with stirring at room temperature to obtain DAS-DTEN-Gd.

Gd concentration (ICP emission spectral analysis): 19 mM

EXAMPLE 6

Synthesis of Gd complex

In to the same manner as in Example 5 except that DAA-DTEN, DAMP-DTEN or DAMP-(AB-DOTA) is used instead of DAS-DTEN, the corresponding Gd complex is obtained.

EXAMPLE 7

Synthesis of DAS-DTEN-Dy

DAS-DTEN (0.2 g, 0.02 mmol) was dissolved in distilled water (3 ml). Dysprocium chloride hexahydrate (0.007 g, 0.018 mmol) was added thereto and the mixture was reacted with stirring at room temperature to obtain DAS-DTEN-Dy.

Dy concentration (ICP emission spectral analysis): 6.5 mM

EXAMPLE 8

Synthesis of Dy complex

In to the same manner as that described in Example 7 except that DAA-DTEN, DAMP-DTEN or DAMP-(AB-DOTA) is used instead of DAS-DTEN, the corresponding Dy complex is obtained.

TEST 1

Relaxivity of DAS-DTEN-Gd (in vitro test)

An appropriate amount of DAS-DTEN-Gd was dissolved in distilled water. The relation to water proton exposed to this compound was determined as a proton relaxation time ($T_1$ and $T_2$, msec.) at room temperature (24° to 26° C.) using NMR (6.35T, manufactured by Nihondenshi K. K., Japan). Respective relaxation times are shown in Table 1.

TABLE 1

| Relaxation time of DAS-DTEN-Gd | | |
|---|---|---|
| Concentration (mM) | $T_1$ (msec.) | $T_2$ (msec.) |
| 2.3 | 55 | 29 |
| 0 | 3275 | 2208 |

DAS-DTEN-Gd (2.3 mM) shortened the $T_1$ and $T_2$ values of water about 60 times and about 76 times, respectively. Relaxivity valves on the $T_1$ and $T_2$ (each $R_1$ or $R_2$ $(mM.S)^{-1}$) were calculated based on the values in Table 1. The results are shown in Table 2.

TABLE 2

| Relaxivity of DAS-DTEN-Gd | | |
|---|---|---|
| Compound | $R_1$ $(mM \cdot S)^{-1}$ | $R_2$ $(mM \cdot S)^{-1}$ |
| DAS-DTEN-Gd | 7.9 | 15.1 |
| DTPA-Gd | 3.9 | 4.8 |

DAS-DTEN-Gd has good in vitro relaxation effect, which is significantly higher than that of DTPA-Gd (also shown in Table 2) measured in the same manner. This clearly shows the effectiveness of the complex compound of the present invention.

TEST 2

Relaxation time in blood in a mouse after intravenous administration of DAS-DTEN-Gd (ex vivo test)

A DAS-DTEN-Gd solution (Gd concentration: 19 mM) was administered to a thiopental-anesthetized ICR female mouse (body weight: 54 g) through the tail vein (the dose of Gd administered: 0.025 mmol/kg). Blood was taken from the aorta descendence at 15 minutes after administration and the relaxation time ($T_1$, msec.) of blood at room temperature (24°–26° C.) was determined with 6.35T NMR (manufactured by Nihondenshi K.K., Japan).

Furthermore, as a control, blood was taken from the aorta descendence of a thiopental-anesthetized ICR female mouse (body weight: 55 g) and, in the same manner, the relaxation time was determined. The results are shown in Table 3.

TABLE 3

| Relaxation time of DAS-DTEN-Gd in blood | |
|---|---|
| | $T_1$ in blood (msec.) |
| Mouse given with DAS-DTEN-Gd | 1292 |
| Control mouse | 1769 |

$T_1$ relaxation time of DAS-DTEN-Gd in the blood is about 1.4 times more effective in comparison with that of the control mouse and it has been found that the relaxation time of blood is effectively shortened.

TEST 3

Contrast enhancement of the heart in a rat immediately after intravenous administration of DAS-DTEN-Gd (in vivo test)

A DAS-DTEN-Gd solution (Gd concentration: 19.0 mM) was administered to a thiopental-anesthetized Sprague-Dawley female rat (body weight: 198 g, 9-weeks old) through a cannula fixed at the femoral vein (the dose of Gd administered: 0.087 mmol/kg). After about 30 seconds, the animal was sacrificed by administration of a pentobarbital solution (1 ml) through the above cannula and fixed in the dorsal position in the magnetic field of a MRI spectrometer. MRI measurement (transverse sectional view) of the chest region including the heart, was carried out.

As a control, a sprague-Dawley female rat (body weight: 188 g, 9-weeks old) was sacrificed by administration of pentobarbital solution (1 ml) through a cannula fixed at the femoral vein and was subjected to the same MRI measurement (transverse sectional view).

The apparatus (SIGNA manufactured by GE, U.S.A.) had a magnetic field intensity of 1.5 T and, as an imaging coil, a 26 cm ϕbird-cage type head QD coil was used. Imaging was carried out according to the spin echo technique of $T_1$ weighted (TR/TE, 600/30 msec)

under conditions of 10 mm in slice thickness, and a resolution of 256×128.

The heart and its vascular system of the rat to which DAS-DTEN-Gd was administered were imaged at high signal intensity, which demonstrated that the effective contrast enhancement was also obtained in vivo. The signal intensity from the heart imaged with DAS-DTEN-Gd was about 4.7 times higher than that of the same part of the heart of the control rat.

TEST 4

Contrast enhancement of the heart in a rat at 30 minutes after intravenous administration of DAS-DTEN-Gd (in vivo test)

A DAS-DTEN-Gd solution (Gd concentration: 19.0 mM) was administered to a thiopental-anesthetized Sprague-Dawley female rat (body weight: 186 g, 9-weeks old) through a cannula fixed at the femoral vein (the dose of Gd administered: 0.087 mmol/kg). The animal was sacrificed by administration of a pentobarbital solution (1 ml) through the above cannula at 30 minutes after administration and fixed in the dorsal position in the magnetic field of a MRI spectrometer. MRI measurement (transverse sectional view) of the chest region including the heart, was carried out.

As a control, DTPA-Gd (MAGNEVIST) was administered to a Sprague-Dawley female rat (body weight: 234 g, 9-weeks old) (0.1 mmol/kg) through a cannula fixed at the femoral vein and MRI measurement (transverse sectional view) of the chest region including the heart was carried out in the same manner.

The apparatus (SIGNA manufactured by GE, U.S.A.) had a the magnetic field intensity of 1.5 T and, as an imaging coil, a 26 cm φbird-cage type head QD coil was used. Imaging was carried out according to the spin echo technique of $T_1$ weighted (TR/TE, 600/30 msec) under the conditions of 10 mm in slice thickness, and a resolution of 256×128.

The signal intensity from the rat to which DAS-DTEN-Gd was administered was found to be about 1.4 times higher than that of the control rat when comparing the signal intensity from the same part of the heart. The superiority in retention in blood of DAS-DTEN-Gd over that of DTPA-Gd together with the dose of Gd demonstrated the advantages of the present invention.

REFERENCE EXAMPLE 1

Radioactivity distribution in a rat after intravenous administration of DAS-DTEN-In-111 (in vivo test)

DAS-DTEN (10 mg) was dissolved in distilled water (0.5 ml) and 0.1M citrate buffer (pH 5.9, 1 ml) was added thereto. The mixture was admixed with an indium chloride (In-111) solution (0.5 ml, 59 MBeq) to obtain DAS-DTEN-In-111. The radiochemical purity was 100%.

Sprague-Dawley female rats (three rats/group) (body weight: 110 to 130 g) were anesthetized with thiopental and DAS-DTEN-In-111 (50 μl/rat) was administered through the tail vein. The animals were sacrificed by dehematization at 0.25, 1, 3, 6 and 24 hours after administration. The main organs were removed and the radioactivity of each organ was measured. The radioactivity distribution ratios in the blood and urine at each measurement time, are shown in Table 4.

TABLE 4

| Radioactivity distribution ratio of DAS-DTEN-In-111 in blood and urine | | |
|---|---|---|
| Time (hr) | Blood (%/dose) | Urine (%/dose) |
| 0.25 | 4.02 ± 0.92 | 48.26 ± 4.42 |
| 1.0 | 2.28 ± 1.18 | 63.74 ± 2.29 |
| 3.0 | 1.15 ± 0.14 | 72.09 ± 2.54 |
| 6.0 | 0.94 ± 0.02 | 74.67 ± 1.98 |
| 24.0 | 0.19 ± 0.10 | 78.33 ± 2.16 |

TABLE 5

| Radioactivity distribution ratio of DAA-DTEN-In-111 in blood and urine | | |
|---|---|---|
| Time (hr) | Blood (%/dose) | Urine (%/dose) |
| 0.25 | 3.77 ± 0.29 | 48.90 ± 3.74 |
| 1.0 | 1.11 ± 0.51 | 72.92 ± 2.10 |
| 3.0 | 0.32 ± 0.05 | 81.76 ± 1.84 |
| 6.0 | 0.19 ± 0.06 | 84.56 ± 1.14 |
| 24.0 | 0.08 ± 0.02 | 86.81 ± 1.87 |

As seen from the results of Table 5, the half-life period of DAA-DTEN-In-111 in the blood was about 45 minutes and was found to be clinically effective retention in the blood. Since excretion into the urine was good, there was no problem of residence in the body.

As seen from the results in Table 4, the half-life period of DAS-DTEN-In-111 in blood was about 2 hours and was found to be clinically effective retention in the blood. Since excretion into the urine was good, there was no problem of residence in the body.

REFERENCE EXAMPLE 2

Radioactivity distribution in rats after intravenous administration of DAA-DTEN-In-111 (in vivo test)

DAA-DTEN (10 mg) was dissolved in distilled water (0.5 ml), followed by addition of 0.1M citrate buffer (pH 5.9) (1 ml). The mixture was admixed with an indium chloride (In-111) solution (0.5 ml, 473 MBeq) to obtain DAA-DTEN-In-111. The radiochemical purity was 100%.

Sprague-Dawley female rats (three rats/group) (body weight: 150 to 190 g) were anesthetized with thiopental and DAA-DTEN-In-111 (25 μl/rat) was administered through the tail vein. The animals were sacrificed by dehematization at 0.25, 1, 3, 6 and 24 hours after administration. The main organs were removed and the radioactivity of each organ was measured. The radioactivity distribution ratios in the blood and urine at each measurement time, are shown in Table 5.

What is claimed is:

1. A nuclear magnetic resonance imaging agent which comprises a complex compound composed of (a) a dialdehyde-saccharide having a molecular weight of from 500 to 10,000, at least one of the constituent monosaccharides of which is oxidation-cleaved, (b) at least one complexing agent which is chemically coupled to an aldehyde group of the dialdehyde-saccharide and (c) a paramagnetic metal ion which is chemically coupled to the complexing agent.

2. The imaging agent according to claim 1, wherein the retention time of the complex compound in blood is from 0.5 to 5 hours as its half-life period in blood.

3. The imaging agent according to claim 2, wherein the constituent monosaccharide in the complex compound is D-glucose.

4. The imaging agent according to claim 2, wherein the number of repetition units of the constituent monosaccharide in the complex compound is from 3 to 10.

5. The imaging agent according to claim 2, wherein the complexing agent in the complex compound is a derivative of diethylenetriaminepentaacetic acid or 1,4,7,10-tetraazacyclododecane-1,4,7,10-tetraacetic acid.

6. The imaging agent according to claim 2, wherein the paramagnetic metal ion in the complex compound is a lanthanide element having the atomic number of from 57 to 70.

7. The imaging agent according to claim 6, wherein the paramagnetic metal ion is Gd or Dy.

8. The imaging agent according to claim 2, wherein the concentration of the paramagnetic metal ion in the complex compound is from $1\times10^{-5}$ to $1\times10$ mol/liter.

* * * * *

UNITED STATES PATENT AND TRADEMARK OFFICE

CERTIFICATE OF CORRECTION

PATENT NO. : 5,271,929

DATED : December 21, 1993

INVENTOR(S) : YUJI HASHIGUCHI ET AL

It is certified that error appears in the above-indentified patent and that said Letters Patent is hereby corrected as shown below:

On the title page, item [75], change "Soedgaura" to --Sodegaura--.

Signed and Sealed this

Tenth Day of May, 1994

Attest:

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : 5,271,929

DATED : December 21, 1993

INVENTOR(S) : YUJI HASHIGUCHI ET AL

It is certified that error appears in the above-identified patent and that said Letters Patent is hereby corrected as shown below:

On the title page, under "Foreign Application Priority Data," delete "173743" and insert -- 3-173743 --.

Signed and Sealed this

Fifteenth Day of November, 1994

Attest:

BRUCE LEHMAN

Attesting Officer

Commissioner of Patents and Trademarks